US012611229B2

(12) United States Patent
Fagan

(10) Patent No.: US 12,611,229 B2
(45) Date of Patent: Apr. 28, 2026

(54) UNIVERSAL FIXATOR CLAMP

(71) Applicant: Orthopedic Designs North America, Inc., Tampa, FL (US)

(72) Inventor: Lance Fagan, Tampa, FL (US)

(73) Assignee: Orthopedic Designs North America, Inc., Tampa, FL (US)

( * ) Notice: Subject to any disclaimer, the term of this patent is extended or adjusted under 35 U.S.C. 154(b) by 107 days.

(21) Appl. No.: 18/612,547

(22) Filed: Mar. 21, 2024

(65) Prior Publication Data

US 2025/0295433 A1     Sep. 25, 2025

(51) Int. Cl.
A61B 17/64          (2006.01)
(52) U.S. Cl.
CPC ................................ A61B 17/6466 (2013.01)
(58) Field of Classification Search
CPC .............. A61B 17/645; A61B 17/6416; A61B 17/6441
See application file for complete search history.

(56) References Cited

U.S. PATENT DOCUMENTS

| | | | | | |
|---|---|---|---|---|---|
| 5,947,671 | A | * | 9/1999 | Kanaan | G05G 1/10<br>74/555 |
| 11,660,122 | B2 | * | 5/2023 | Ziran | A61B 17/6458<br>606/59 |
| 2002/0026190 | A1 | * | 2/2002 | Walulik | A61B 17/645<br>606/57 |

| | | | | | |
|---|---|---|---|---|---|
| 2002/0165543 | A1 | * | 11/2002 | Winquist | A61B 17/6466<br>606/54 |
| 2003/0181911 | A1 | * | 9/2003 | Venturini | A61B 17/6466<br>606/56 |
| 2006/0287652 | A1 | * | 12/2006 | Lessig | A61B 17/6458<br>606/54 |
| 2007/0038217 | A1 | * | 2/2007 | Brown | A61B 17/6466<br>606/57 |
| 2011/0087226 | A1 | * | 4/2011 | Murner | A61B 17/6466<br>606/54 |
| 2012/0150180 | A1 | * | 6/2012 | Verma | A61B 17/6416<br>606/59 |
| 2012/0150182 | A1 | * | 6/2012 | Dominik | A61B 17/60<br>606/59 |
| 2012/0296335 | A1 | * | 11/2012 | Mullaney | A61B 17/6466<br>606/59 |
| 2014/0257287 | A1 | * | 9/2014 | Chang | A61B 17/6475<br>606/58 |

(Continued)

*Primary Examiner* — Jacqueline T Johanas
(74) *Attorney, Agent, or Firm* — Carlson IP Law, LLC

(57) ABSTRACT

An external fixation system that uses a torquing apparatus and a universal fixator clamp. The universal fixator clamp comprises a proximal head, a screw plate, a first upper clamp plate, a second upper clamp plate, a spring, a first lower clamp plate, and a second lower clamp plate. The first upper clamp plate and second upper clamp plate define at least one bone pin channel and at least one frame rod channel. The first lower clamp plate and second lower clamp plate define at least one bone pin channel and at least one frame rod channel. A central bolt engages with the screw plate to compress the universal fixator clamp when turned by the torquing apparatus. The torquing apparatus has a plurality of arms that engage with complementary recesses in the proximal head to prevent patients from disengaging the clamp once tightened.

6 Claims, 8 Drawing Sheets

(56) References Cited

U.S. PATENT DOCUMENTS

| | | | |
|---|---|---|---|
| 2014/0257288 A1* | 9/2014 | Chang ................. | A61B 17/645 |
| | | | 606/59 |
| 2016/0192964 A1* | 7/2016 | Lorenzini .......... | A61B 17/6466 |
| | | | 606/59 |
| 2017/0252069 A1* | 9/2017 | Muniz ................ | A61B 17/6466 |
| 2017/0281236 A1* | 10/2017 | Mussolin ........... | A61B 17/6466 |
| 2018/0132897 A1* | 5/2018 | Shiner .................... | A61B 17/64 |
| 2019/0110814 A1* | 4/2019 | Nemovicher ......... | A61B 90/57 |
| 2019/0183531 A1* | 6/2019 | Miller ................ | A61B 17/6466 |
| 2020/0367935 A1* | 11/2020 | Venturini ........... | A61B 17/6475 |
| 2021/0100585 A1* | 4/2021 | Kent .................. | A61B 17/6466 |
| 2021/0267805 A1* | 9/2021 | Sanders, Jr. .......... | A61B 17/60 |
| 2022/0226022 A1* | 7/2022 | Venturini .......... | A61B 17/6466 |
| 2022/0296278 A1* | 9/2022 | Ziran ................. | A61B 17/6466 |
| 2023/0363795 A1* | 11/2023 | Höntzsch .......... | A61B 17/6466 |
| 2024/0188993 A1* | 6/2024 | Kraus ............... | A61B 17/6483 |
| 2024/0341812 A1* | 10/2024 | Fabri .................... | A61B 17/64 |
| 2025/0040962 A1* | 2/2025 | Schiffers ........... | A61B 17/6416 |

* cited by examiner

UNIVERSAL FIXATOR CLAMP

FIELD OF THE INVENTION

This invention relates to an orthopedic clamp. Specifically, the described invention relates to a fixator clamp
system used to help stabilize fractures in patients using an
external torquing apparatus to prevent a patient from loos-
ening the clamp once tightened.

DESCRIPTION OF BACKGROUND ART

The use of external fixators is well known in the medical
field of orthopedics when there is a need for stabilizing bone
fractures. These fixators are generally used in place of
conventional plaster casts. External fixators generally com-
prise a plurality of threaded bone pins, or screws, normally
in pairs, which are implanted in the bone fragments of the
fracture in such a way that the head ends of the bone pins
project from the skin of the patient. The ends are connected
to a rigid external frame which is equipped with clamps and
rods, which can be orientated in such a way as to allow them
to be adjusted to the position of the bone pins.

Bone pins generally have a cylindrical body with a
threaded end designed to be screwed into a bone fragment
and a head end designed to be connected to a temporary grip
that allows the pin to be screwed into the bone fragment. A
description of how the bone pins reach alignment when
applied to a patient is described in U.S. Pat. No. 11,660,122,
which is incorporated herein by reference.

Several types of universal clamps have been developed
over the years. For example, the external fixator described in
U.S. Pat. No. 11,660,122 incorporates a plurality of collaps-
ible turn levers, each turn lever having a longitudinal body
extending between a movable end and a hinged end, the
knob having a central screw turn actuator with an outer side
and an inner side, the hinged end of each turn lever being
connected via a hinge to the outer side of the central screw
turn actuator, the movable end of each turn lever being
movable between a collapsed position where each lever is
situated over the outer side of the central screw turn actuator
and an open position where the movable end is situated
outwardly from the outer side of the central screw turn
actuator, the central screw turn actuator engaged with the
clamp screw to permit rotation of the central screw turn
actuator relative to and movement along the cylindrical
threaded body when rotational force is applied in first and
second rotational directions to the torque amplifying knob in
order to permit relative movement of the first clamp and the
second clamp. A primary disadvantage of this clamp design
is that a patient who is uncomfortable with how his limb
feels may make the decision to engage the collapsible turn
levers and loosen the clamp thereby allowing the bone pins
to move which would then potentially cause damage to the
healing process.

Therefore, it is an object of this invention to provide an
improvement which overcomes the aforementioned inad-
equacies of the prior art devices and provides an improve-
ment which is a significant contribution to the advancement
of the universal fixator clamp art.

Another object of this invention is to provide a low-cost
clamp made of readily available materials such as plastic.

Another object of this invention is to provide a clamp that
cannot be undone by hand.

Another object of this invention is to provide a sterile
device that can be used outside of a surgical setting if
needed.

The foregoing has outlined some of the pertinent objects
of the invention. These objects should be construed to be
merely illustrative of some of the more prominent features
and applications of the intended invention. Many other
beneficial results can be attained by applying the disclosed
invention in a different manner or modifying the invention
within the scope of the disclosure. Accordingly, other
objects and a fuller understanding of the invention may be
had by referring to the summary of the invention and the
detailed description of the preferred embodiment in addition
to the scope of the invention defined by the claims taken in
conjunction with the accompanying drawings.

SUMMARY OF THE INVENTION

The long-standing but heretofore unfulfilled need for an
apparatus that overcomes the limitations of the prior art is
now met by a new, useful, and non-obvious invention. The
invention meets the need for a new universal fixator clamp
that overcomes the issues inherent in the prior art.

The present invention relates generally to an external
fixation system that uses a torquing apparatus and a univer-
sal fixator clamp. The universal fixator clamp comprises a
proximal head, a screw plate, a first upper clamp plate, a
second upper clamp plate, a spring, a first lower clamp plate,
and a second lower clamp plate. The first upper clamp plate
and second upper clamp plate define at least one bone pin
channel and at least one frame rod channel. The first lower
clamp plate and second lower clamp plate define at least one
bone pin channel and at least one frame rod channel. A
central bolt engages with the screw plate to compress the
universal fixator clamp when turned by the torquing appa-
ratus. The torquing apparatus has a plurality of arms that
engage with complementary recesses in the proximal head to
prevent patients from disengaging the clamp once tightened.

The foregoing has outlined rather broadly the more per-
tinent and important features of the present invention in
order that the detailed description of the invention that
follows may be better understood so that the present con-
tribution to the art can be more fully appreciated. Additional
features of the invention will be described hereinafter which
form the subject of the claims of the invention. It should be
appreciated by those skilled in the art that the conception and
the specific embodiment disclosed may be readily utilized as
a basis for modifying or designing other structures for
carrying out the same purposes of the present invention. It
should also be realized by those skilled in the art that such
equivalent constructions do not depart from the spirit and
scope of the invention as set forth in the appended claims.

BRIEF DESCRIPTION OF THE DRAWINGS

For a more complete understanding of the present disclo-
sure and its advantages, reference is now made to the
following descriptions, taken in conjunction with the accom-
panying drawings, in which.

Similar reference numerals refer to similar parts throughout the several views of the drawings. The components of the drawings are not necessarily to scale, emphasis instead being placed upon clearly illustrating the principles of the present disclosure.

DETAILED DESCRIPTION OF THE DRAWINGS

The following description is of the best mode presently contemplated for carrying out the invention. This description is not to be taken in a limiting sense but is made merely for the purpose of describing one or more preferred embodiments of the invention. The scope of the invention should be determined with reference to the claims.

Figure 1:
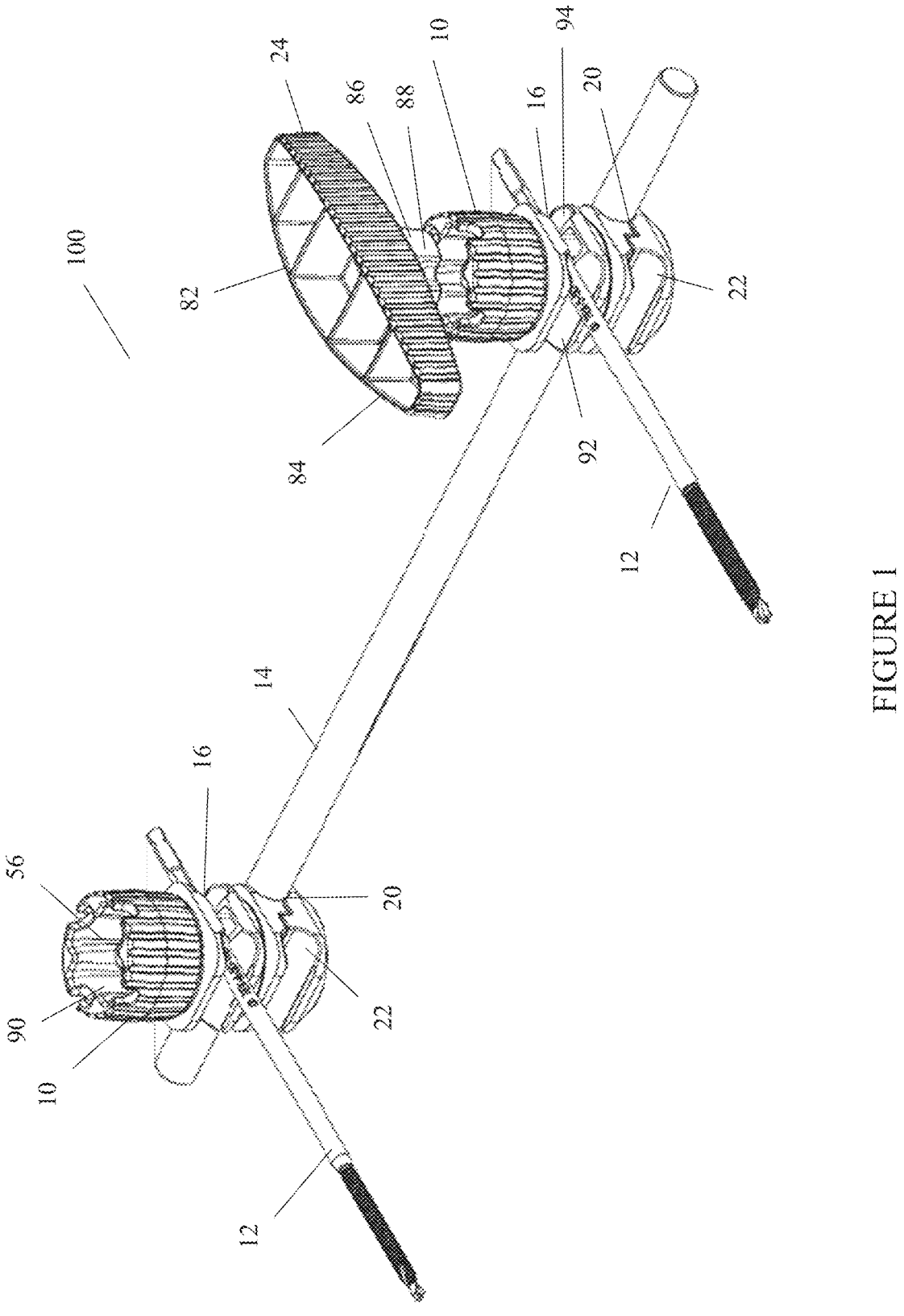
FIG. 1 is a perspective view of an embodiment of the
universal fixator clamp of the present invention.
Figure 4:
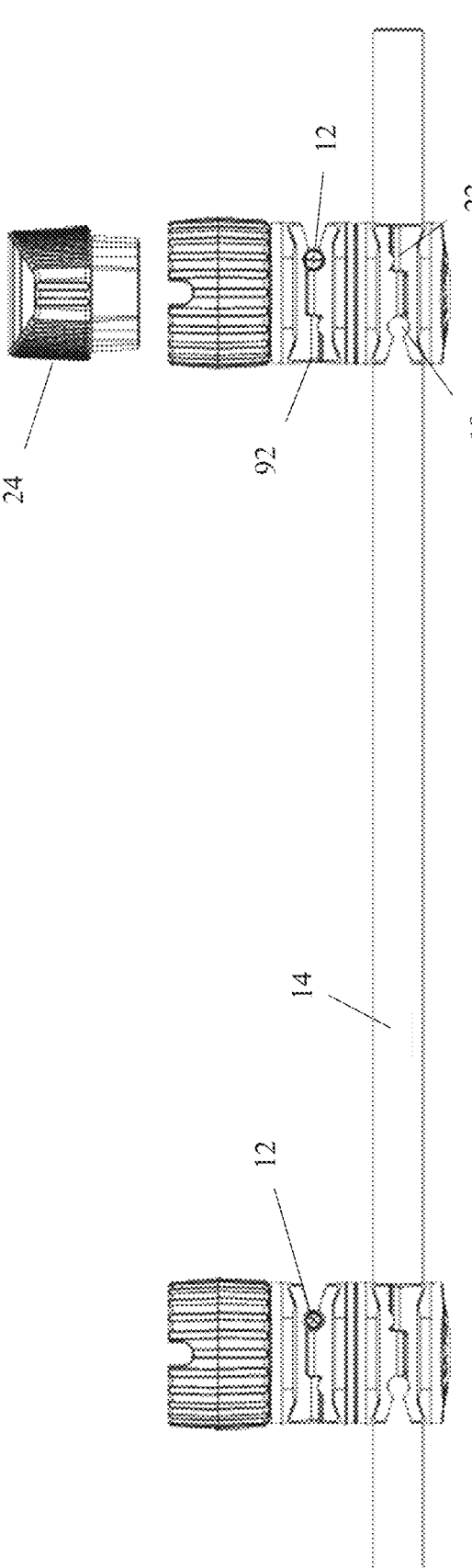
FIG. 4 is a front perspective view of an embodiment of the
universal fixator clamp of the present invention engaged
with bone pins and a frame rod.

A first embodiment of the present invention is seen in FIG. 1. The universal fixator clamp 10 is used as part of the external fixation system 100 which comprises the universal fixator clamp 10, at least one bone pin 12, and at least one frame rod 14. The universal fixator clamp 10 has a first bone pin channel 16, and second bone pin channel 18 (as seen in FIG. 4) as well as a first frame rod channel 20 and second frame rod channel 22. Having multiple channels for each of the bone pin 12 and frame rod 14 allows for more precise placement when engaging the clamp and allows for the use of more than one bone pin 12 or frame rod 14 if needed. Alternatively, an embodiment may have a third frame rod channel 92 and fourth frame rod channel 94 if further structure is needed.

Figure 2:
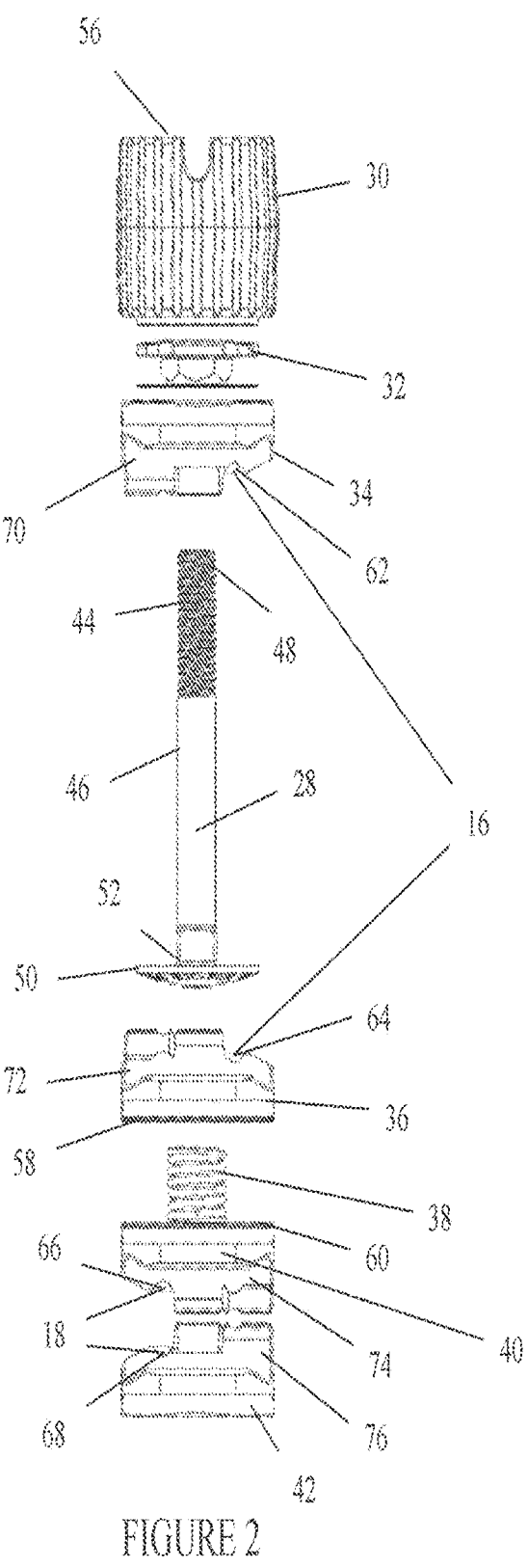
FIG. 2 is an exploded view of the clamp body of the
present invention.
Figure 3:
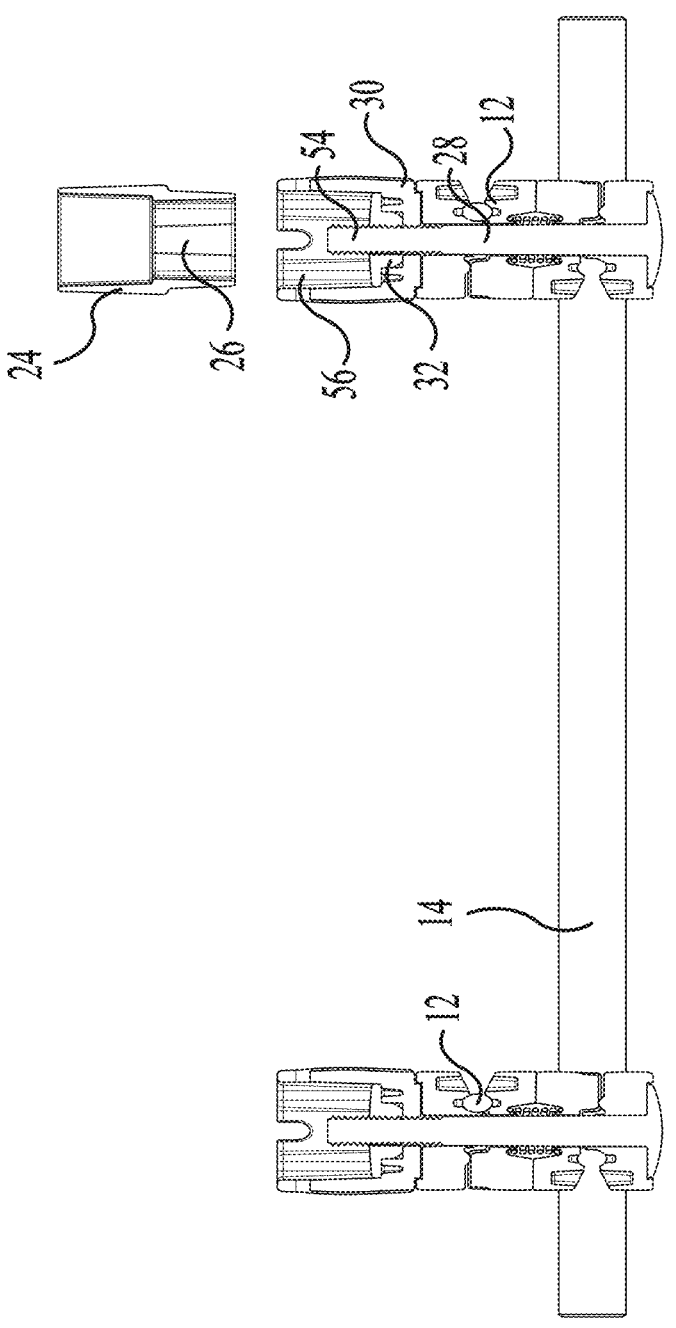
FIG. 3 is a cross-sectional view of the clamp body of the
present invention engaged with a bone pin and frame rod.

As shown in FIG. 2 and FIG. 3, the universal fixator clamp 10 is compressed using a torquing apparatus 24 that mates with the universal fixator clamp 10. The torquing apparatus 24 has an internal threaded engagement channel 26 designed to receive an internal bolt 28 centrally located within the universal fixator clamp 10.

The universal fixator clamp 10, as shown in FIG. 2 and FIG. 3, comprises a proximal head 30, a screw plate 32, a first upper clamp plate 34, a second upper clamp plate 36, a spring 38, a first lower clamp plate 40, and a second lower clamp plate 42. The first bone pin channel 16 is formed when the first upper clamp plate 34 and second upper clamp plate 36 are clamped together and the second bone pin channel 18 is formed when the first lower clamp plate 40 and second lower clamp plate 42 are clamped together. The first upper clamp plate 34 has a curved top bone pin channel 62 and the second upper clamp plate 36 has a curved bottom bone pin channel 64 that creates the first bone pin channel 16. The second bone pin channel 18 is formed from a curved lower bone pin channel 66 and a curved bottom bone pin channel 68 in the first lower clamp plate 40 and second lower clamp plate 42 respectively. In a similar vein, the first frame rod channel 20 and second frame rod channel 22 are formed when the first lower clamp plate 40 and the second lower clamp plate 42 are clamped together. The first upper clamp plate 34, second upper clamp plate 36, first lower clamp plate 40, and second lower clamp plate 42 each have at least one curved partial frame rod channel 70, 72, 74, 76 that form the first frame rod channel 20 and the second frame rod channel 22.

This clamping action is created by the internal bolt 28 having a threaded body portion 44 which may be the entire length of the bolt body 46 or only at the proximal bolt end 48 and where the internal bolt 28 has a head 50 at a distal end 52. Screw plate 32 threads onto the threaded body portion 44 such that the proximal bolt end 48 has torque head engaging threads 54 that extend into the head cavity 56 of the proximal head 30. These engaging threads 54 are what engage with the torquing apparatus 24 to tighten the universal fixator clamp 10 and hold bone pin 12 and frame rod 14 in place.

Figure 5:
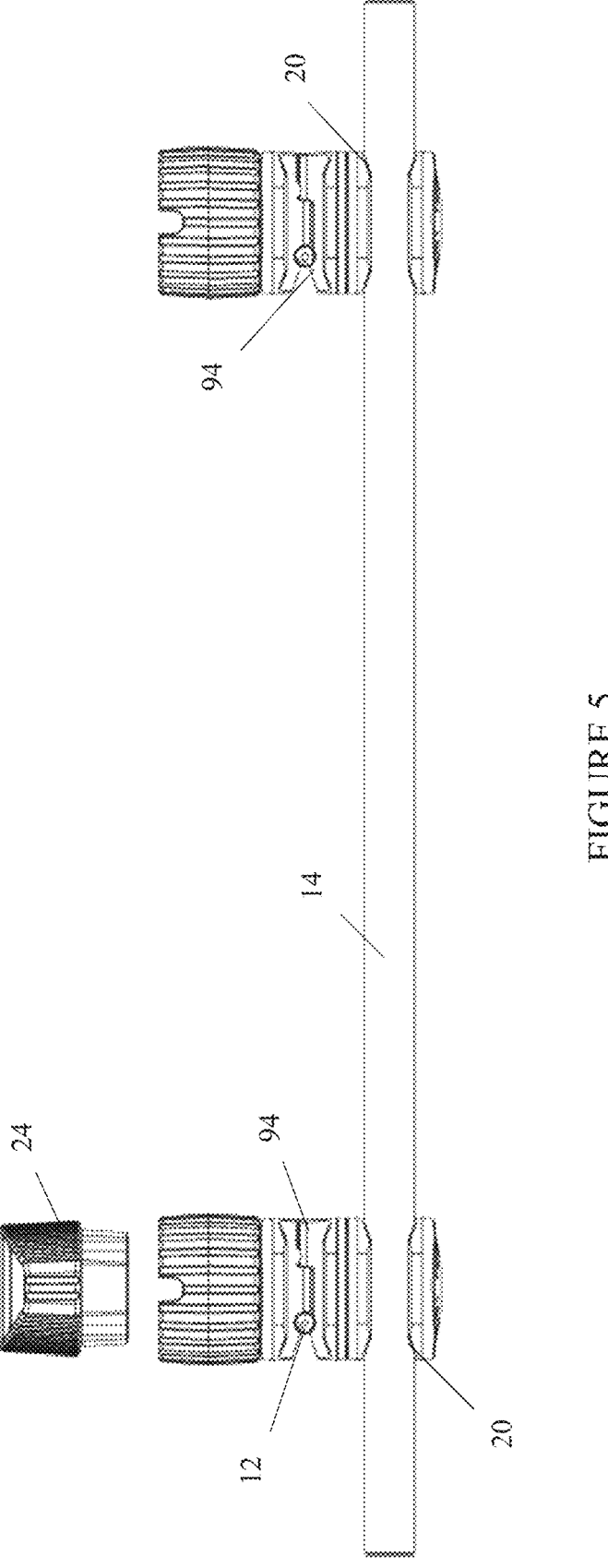
FIG. 5 is a rear perspective view of an embodiment of the universal fixator clamp of the present invention engaged with bone pins and a frame rod.

The second upper clamp plate 36 has a planar bottom face 58 and the first lower clamp plate 40 has a planar top face 60 such that when pressure is applied by rotation of the torquing apparatus 24 there is no gap between the planar bottom face 58 and the planar top face 60, as seen in FIG. 4 and FIG. 5.

Figure 6:
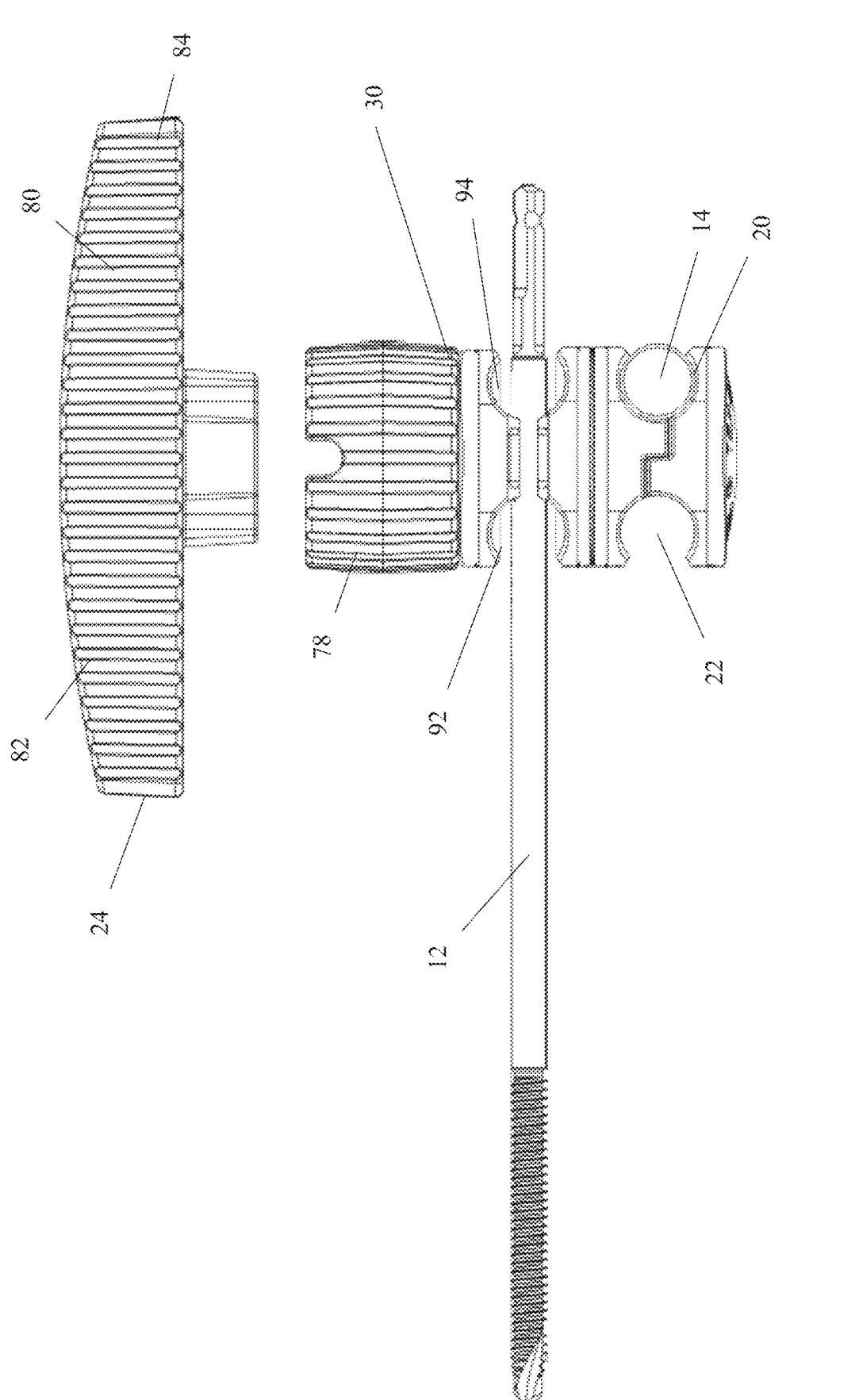
FIG. 6 is a side perspective view of an embodiment of the universal fixator clamp of the present invention engaged with bone pins and a frame rod.
Figure 7:
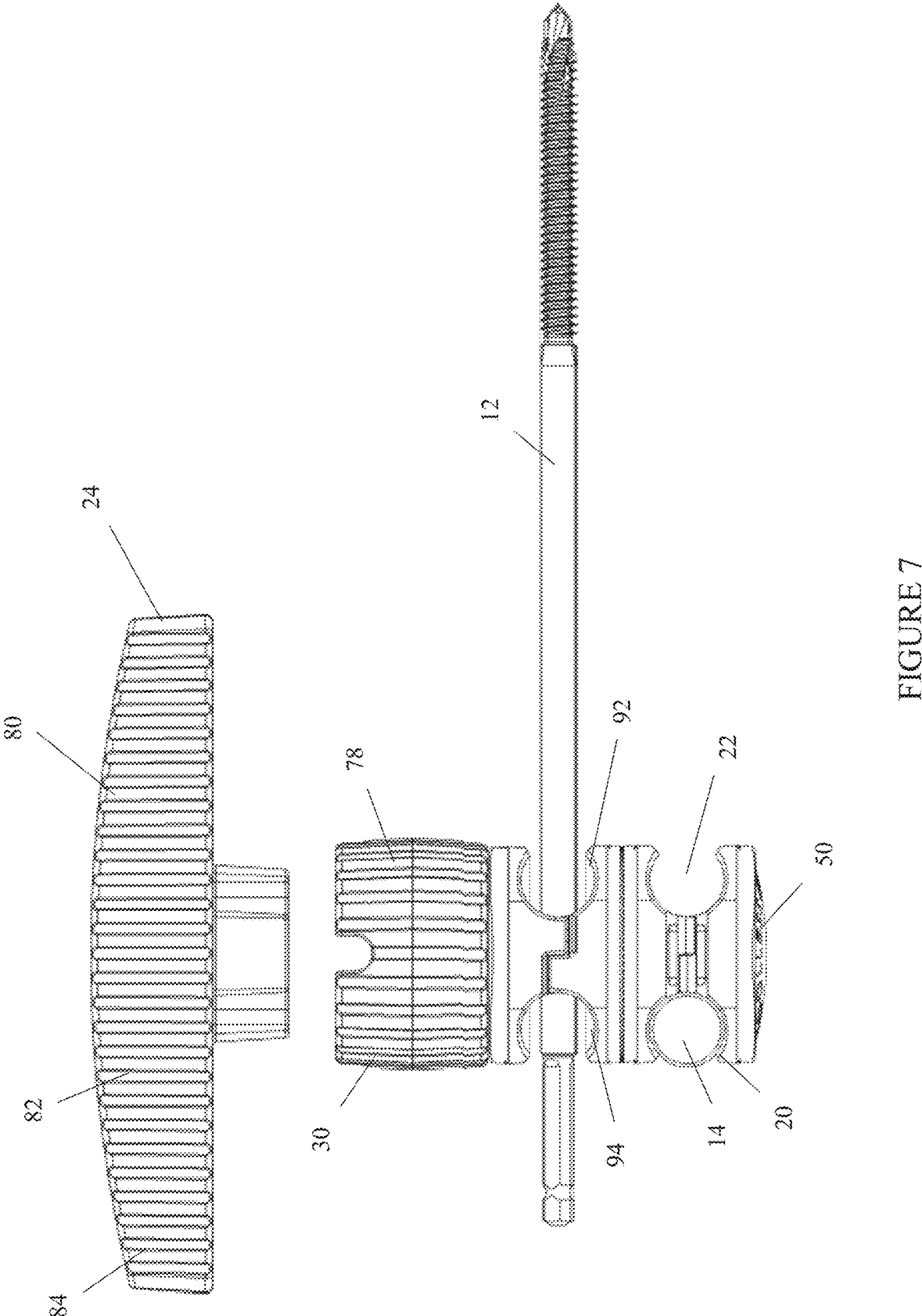
FIG. 7 is an alternative side perspective view of an embodiment of the universal fixator clamp of the present invention engaged with bone pins and a frame rod.
Figure 8:
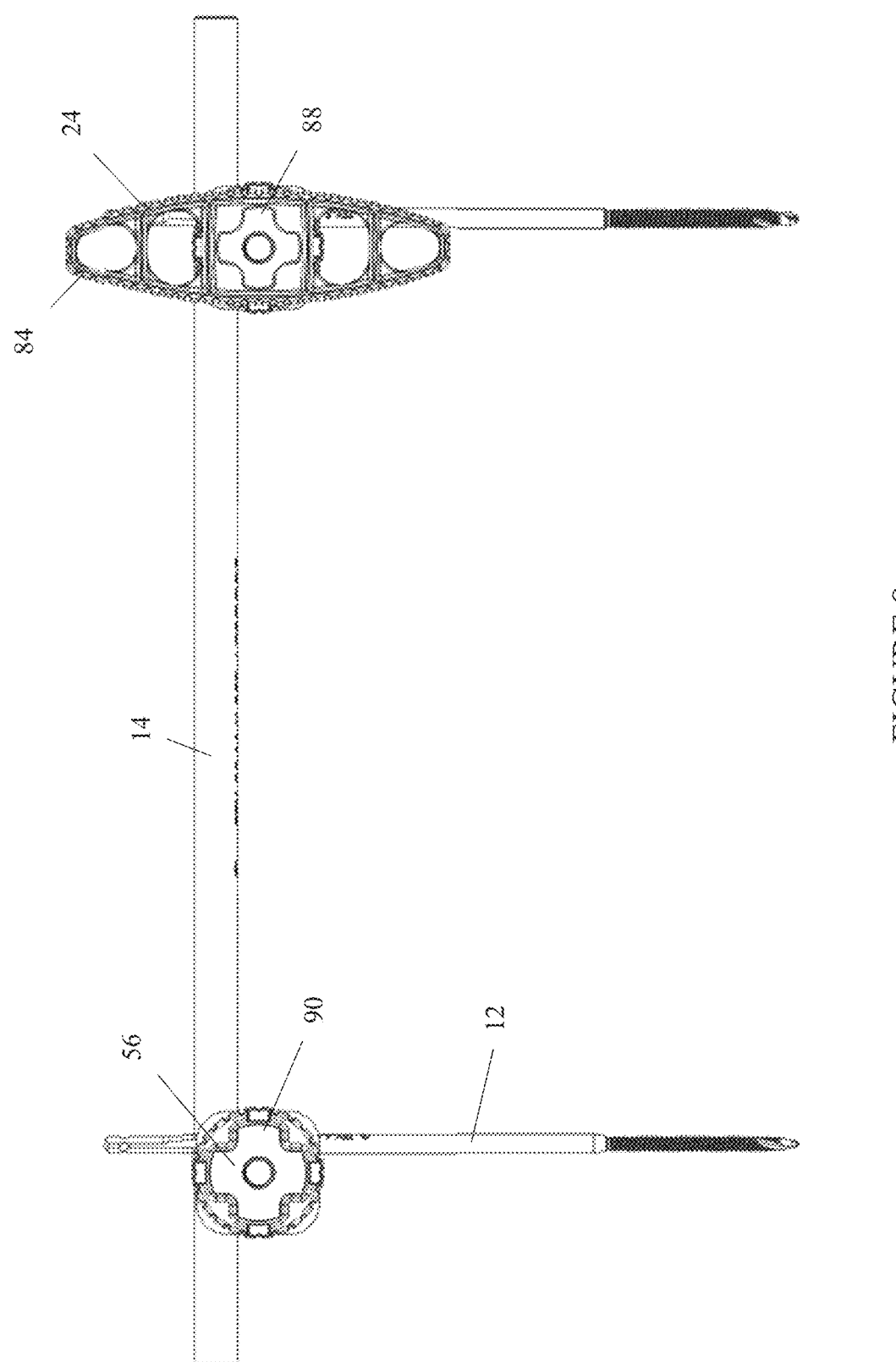
FIG. 8 is a top perspective view an embodiment of the universal fixator clamp of the present invention engaged with bone pins and a frame rod.

As seen in more detail in FIG. 6 and FIG. 7, the proximal head 30 has a plurality of ridges 78 that create a grip point when tightening the universal fixator clamp 10. Likewise, the torquing apparatus 24 has a plurality of torquing ridges 80 that may extend the length of the handle 82 or only at the distal ends 84. The torquing apparatus 24 further includes a proximal head interface 86 that, as seen in FIG. 8, comprises a plurality of arms 88. Preferably, there are four arms 88 in a clover shape but the proximal head interface 86 can have five (star pattern), six (hexagonal), or eight (octagonal) arms 88. The arms 88 of torquing apparatus 24 engage with the complementarily shaped head cavity 56. This means that if there are, for example, four arms 88 then the head cavity 56 has four recessions 90 for each arm 88. Preferably, four arms 88 are in use because an increase in the number of arms 88 can increase the likelihood that the recessions 90 get stripped if too much pressure is applied.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. An external orthopedic fixation system comprising:
   a torquing apparatus further comprising lateral handles having a plurality of ridges, a proximal head interface having a plurality of arms, and an internal threaded engagement channel;
   a universal fixator clamp further comprising a proximal head having a proximal head void with a plurality of recessions, a screw plate, a first upper clamp plate comprising a top bone pin channel and a first curved partial frame rod channel, a second upper clamp plate having a curved bottom bone pin channel and a second curved partial frame rod channel, a spring, a first lower clamp plate having a curved lower bone pin channel and a third curved partial frame rod channel, and a second lower clamp plate having a curved bottom bone pin channel and a fourth curved partial frame rod channel;
   wherein the universal fixator clamp is secured with an internal bolt that threads into the screw plate, the internal bolt further comprising a bolt body having a proximal bolt end and a distal bolt end, a head at the distal bolt end, and a threaded body portion at the proximal bolt end, the threaded body portion engaging with the screw plate and extending through the screw plate, and wherein the torquing apparatus causes the screw plate to engage with the threaded body portion during rotation thereby compressing the first upper clamp plate, second upper clamp plate, first lower clamp plate, and second lower clamp plate together;

at least one bone pin inserted into a first bone pin channel or a second bone pin channel with a first bone pin channel formed from the top bone pin channel and bottom bone bin channel and a second bone pin channel formed from the lower pin channel and the bottom bone pin channel; and at least one frame rod inserted into a frame rod channel with a first frame rod channel formed from the first curved partial frame rod channel in the first upper clamp plate and the second curved partial frame rod channel in the second upper clamp plate and a second frame rod channel formed from the third curved partial frame rod channel in the first lower clamp plate and the fourth curved partial frame rod channel in the second lower clamp plate.

2. The external orthopedic fixation system of claim 1 wherein the torquing apparatus and the universal fixator clamp are made of plastic.

3. The external orthopedic fixation system of claim 1 wherein the proximal head further comprises a plurality of ridges on an external face.

4. The external orthopedic fixation system of claim 1 wherein the threaded body portion of the internal bolt extends the entire length of the internal bolt.

5. The external orthopedic fixation system of claim 1 wherein the threaded body portion of the internal bolt partially extends from the proximal bolt end towards the distal bolt end.

6. The external orthopedic fixation system of claim 1 wherein the second upper clamp plate has a planar bottom face and the first lower clamp plate has a planar top face such that when pressure is applied by rotation of the torquing apparatus there is no gap between the planar bottom face and the planar top face.

* * * * *